United States Patent
Hinderer et al.

(10) Patent No.: US 8,546,328 B2
(45) Date of Patent: *Oct. 1, 2013

(54) LIQUID FORMULATION OF G-CSF CONJUGATE

(75) Inventors: Walter Hinderer, Rodgau (DE); Christian Scheckermann, Ehrenkirchen (DE)

(73) Assignee: BioGeneriX AG, Mannheim (DE)

( * ) Notice: Subject to any disclaimer, the term of this patent is extended or adjusted under 35 U.S.C. 154(b) by 373 days.

This patent is subject to a terminal disclaimer.

(21) Appl. No.: 12/675,749

(22) PCT Filed: Aug. 27, 2008

(86) PCT No.: PCT/EP2008/061232
§ 371 (c)(1),
(2), (4) Date: Feb. 26, 2010

(87) PCT Pub. No.: WO2009/027437
PCT Pub. Date: Mar. 5, 2009

(65) Prior Publication Data
US 2011/0053844 A1   Mar. 3, 2011

(30) Foreign Application Priority Data
Aug. 27, 2007   (EP) .................................. 07115047

(51) Int. Cl.
*A61K 38/19* (2006.01)
*C07K 14/53* (2006.01)
*C07K 1/107* (2006.01)
*A61M 5/178* (2006.01)
*A61M 5/28* (2006.01)
*A61M 5/32* (2006.01)
*A61J 1/00* (2006.01)

(52) U.S. Cl.
USPC ............ 514/7.6; 530/399; 530/402; 530/421; 604/187; 604/192; 604/403

(58) Field of Classification Search
None
See application file for complete search history.

(56) References Cited

U.S. PATENT DOCUMENTS

| 5,503,827 | A * | 4/1996 | Woog et al. | 424/85.1 |
|---|---|---|---|---|
| 5,874,075 | A | 2/1999 | Collins et al. | |
| 6,555,660 | B2 | 4/2003 | Nissen et al. | |
| 7,338,933 | B2 | 3/2008 | DeFrees et al. | |
| 7,662,933 | B2 | 2/2010 | Kinstler et al. | |
| 7,893,019 | B2 | 2/2011 | Tonon et al. | |
| 8,207,112 | B2 * | 6/2012 | Hinderer et al. | 514/7.6 |
| 2004/0037803 | A1 * | 2/2004 | Sato | 424/85.1 |
| 2004/0039255 | A1 * | 2/2004 | Simonsen et al. | 600/300 |
| 2005/0250678 | A1 * | 11/2005 | DeFrees et al. | 514/8 |
| 2007/0009478 | A1 * | 1/2007 | Germansen et al. | 424/85.1 |
| 2008/0026046 | A1 * | 1/2008 | Skufca et al. | 424/450 |
| 2009/0247450 | A1 | 10/2009 | Mack | |

FOREIGN PATENT DOCUMENTS

| EP | 1260230 | 11/2002 |
|---|---|---|
| WO | WO 94/05332 | 3/1994 |
| WO | WO 2005/039620 | 5/2005 |
| WO | WO 2005/042024 | 5/2005 |
| WO | WO 2005/055946 | 6/2005 |
| WO | WO 2006/074467 | 7/2006 |
| WO | WO 2007/099145 | 9/2007 |
| WO | WO 2008/124406 | 10/2008 |

OTHER PUBLICATIONS

Piedmont, D.M., et al., "Formulation of Neulasta ® (pegfilgrastim)", Advanced Drug Delivery Reviews, vol. 60, p. 50-58, 2007.
Schneider, et al., "A Role for G-CSF (Granulocyte-Colony Stimulating Factor) in the Central Nervous System", Cell Cycle, vol. 4(12), p. 1753-1757, 2005.
Defrees, Shawn et al., "GlycoPEGylation of recombinant therapeutic proteins produced in *Escherichia Coli*", Glycobiology vol. 16, No. 9, pp. 833-843, 2006.
Merlin, Etienne et al., "Letter to the Editor: The pros and cons of split dose granulocyte colony-stimulating factor alone rather than a single high dose for hematopoietic progenitor cell mobilization in small children (< 15 kg )with small tumors", Haematologica, The Hematology Journal, 91(7, 2005), p. 1004-1005.
Office Action, mailed in corresponding Japanese Application No. 2010-522361 on Dec. 11, 2012, 3 pages.
English translation of Office Action mailed in corresponding Japanese Application No. 2010-522361 on Dec. 11, 2012, 3 pages.
Solaroglu, Ihsan et al., "A Novel Neuroprotectant Granulocyte-Colony Stimulating Factor", Stroke, 37: 1123-1128, 2006.

* cited by examiner

*Primary Examiner* — Elizabeth C Kemmerer
*Assistant Examiner* — Regina M Deberry
(74) *Attorney, Agent, or Firm* — Davis Wright Tremaine LLP

(57) ABSTRACT

The present invention relates to a liquid pharmaceutical composition comprising a granulocyte colony stimulating factor polypeptide conjugated with a polymer, the composition having a pH value in the range of 4.5 to 5.5. The composition further comprises a surfactant and optionally one or more other pharmaceutically acceptable excipients. Further, the composition of the invention is free from tartaric acid or salts thereof and from succinic acid and salts thereof as buffering agents and does not contain amino acids as stabilizer. The composition has a good storage stability and is especially useful for the prophylaxis and treatment of disorders and medical indications where granulocyte colony stimulating factor preparations are considered as useful remedies.

30 Claims, No Drawings

SEQUENCE LISTING

```
<160> NUMBER OF SEQ ID NOS: 2

<210> SEQ ID NO 1
<211> LENGTH: 175
<212> TYPE: PRT
<213> ORGANISM: Homo sapiens
<220> FEATURE:
<221> NAME/KEY: MISC_FEATURE
<222> LOCATION: (1)..(175)
<223> OTHER INFORMATION: wild-type amino acid sequence of human
      methionyl-G-CSF as produced in E. coli; threonine residue at
      position 134

<400> SEQUENCE: 1

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160
```

-continued

```
Phe Leu Glu Val Ser Tyr Arg Val Leu Arg His Leu Ala Gln Pro
                165                 170                 175

<210> SEQ ID NO 2
<211> LENGTH: 174
<212> TYPE: PRT
<213> ORGANISM: Homo sapiens
<220> FEATURE:
<221> NAME/KEY: MISC_FEATURE
<222> LOCATION: (1)..(174)
<223> OTHER INFORMATION: amino acid sequence of human G-CSF as produced
      in mammalian cells; threonine residue at position 133

<400> SEQUENCE: 2

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

LIQUID FORMULATION OF G-CSF CONJUGATE

CROSS-REFERENCE TO RELATED APPLICATIONS

The present application is a U.S. National Stage entry under 35 U.S.C. §371 of International Application No. PCT/EP08/61232, filed on Aug. 27, 2008, designating the United States of America and published in English on Mar. 5, 2009, which in turn claims priority to EPO 07115047.8, filed on Aug. 27, 2007, each of which is hereby incorporated by reference in its entirety.

The present invention relates to a liquid pharmaceutical composition comprising a granulocyte colony stimulating factor polypeptide conjugated with a polymer, the composition having a pH value in the range of 4.5 to 5.5. The composition further comprises a surfactant and optionally one or more other pharmaceutically acceptable excipients. Further, the composition of the invention is free from tartaric acid or salts thereof and from succinic acid and salts thereof as buffering agents and does not contain amino acids as stabilizer. The composition shows a good storage stability and is especially useful for the prophylaxis and treatment of disorders and medical indications where granulocyte colony stimulating factor preparations areconsidered as useful remedies.

Granulocyte colony stimulating factor (G-CSF) is a hematopoietic growth factor that stimulates the proliferation and differentiation of hematopoietic precursor cells and the activation of mature neutrophils. G-CSF is capable of supporting neutrophil proliferation in vitro and in vivo. The human form of G-CSF was cloned by groups from Japan and the USA in 1986 (see e.g. Nagata et al. (1986) Nature 319: 415-418). The natural human glycoprotein exists in two forms, one having 174 and the other having 177 amino acids. The more abundant and more active 174 amino acid form has been used in the development of pharmaceutical products by recombinant DNA technology.

Large quantities of recombinant G-CSF have been produced in genetically engineered *Escherichia coli* and have been successfully used in clinical applications to treat cancer patients suffering from chemotherapy-induced neutropenia. *Escherichia coli*-produced G-CSF is a 175 amino acid polypeptide chain containing an extra methionine at its N-terminus This protein has been produced by expressing a G-CSF gene in *E. coli* and purifying the protein product to homogeneity. It is a hydrophobic protein that has five cysteine residues, four of them are involved in disulphide bonding. The free cysteine residue is generally implicated in the formation of higher molecular weight aggregates upon storage in solution. Aggregates of the proteins can also be formed from oxidized forms of the protein that arise by oxidation of the internal methionine residues in the primary sequence of the protein. Of the four methionine residues, one is at the N-terminus and the other three are internal. The oxidized forms of the protein that contain oxidized methionine at position 122 can be separated from the forms containing oxidized methionines at positions 127 or 138 and the native protein by regular reverse phase HPLC separation procedures (the positions are calculated for the Methionyl-G-CSF consisting of 175 amino acids).

The recombinant human G-CSF synthesized in an *E. coli* expression system is called filgrastim (international non-proprietary name, INN). The structure of filgrastim differs slightly from the natural glycoprotein. The other form of recombinant human G-CSF is called lenograstim (INN) and is synthesized in Chinese hamster ovary (CHO) cells. Filgrastim and lenograstim are marketed in Europe under the trade names Neupogen® and Granocyte, respectively.

However, the commercially available forms of recombinant human G-CSF have a short-lived pharmacological effect and often must be administered more than once a day for the duration of the leukopenic state. A molecule with longer circulation half-life would decrease the number of administrations necessary to alleviate the leukopenia and prevent consequent infections. Another problem with currently available recombinant human G-CSF products is the occurrence of dose-dependent bone pain. Since bone pain is experienced by patients as a significant side-effect of treatment with recombinant human G-CSF, it would be desirable to provide a recombinant human G-CSF product that does not cause bone pain, either by means of a product that inherently does not have this effect or that is effective in a dose that is sufficiently small so that no, or at least less, bone pain is caused. Thus, there is clearly a need for improved recombinant G-CSF molecules and pharmaceutical preparations containing G-CSF molecules as stable ready-to-use preparations.

Protein-engineered variants of human G-CSF have been reported, e.g. in G-CSF variants are described in WO 01/87925, EP 0 456 200 A, U.S. Pat. No. 6,166,183, U.S. Pat. No. 6,004,548, U.S. Pat. No. 5,580,755, U.S. Pat. No. 5,582, 823, U.S. Pat. No. 5,675,941, U.S. Pat. No. 5,416,195, U.S. Pat. No. 5,399,345, WO 2005/055946 and WO 2006/074467.

Modification of human G-CSF and other polypeptides so as to introduce at least one additional carbohydrate chain as compared to the native polypeptide has also been reported (U.S. Pat. No. 5,218,092). In addition, polymer modifications of native human G-CSF, including attachment of poly(ethylene glycol) (PEG) groups, have been reported and studied (U.S. Pat. No. 5,824,778, U.S. Pat. No. 5,824,784, WO 96/11953, WO 95/21629 and WO 94/20069).

It is generally accepted that the stability of proteins can be improved and the immune response against these proteins reduced when these proteins are coupled to polymeric molecules. WO 94/28024 discloses that physiologically active proteins modified with PEG exhibit reduced immunogenicity and antigenicity and circulate in the bloodstream considerably longer than unconjugated proteins, i.e. have a reduced clearance rate.

The attachment of synthetic polymers to the peptide backbone in an attempt to improve the pharmacokinetic properties of glycoprotein therapeutics is known in the art. An exemplary polymer that has been conjugated to peptides is PEG. The use of PEG to derivatize peptide therapeutics has been demonstrated to reduce the immunogenicity of the peptides. For example, U.S. Pat. No. 4,179,337 discloses non-immunogenic polypeptides such as enzymes and peptide hormones coupled to PEG or poly(propylene glycol) (PPG). In addition to reduced immunogenicity, the clearance time in circulation is prolonged due to the increased size of the PEG-conjugate of the polypeptides in question.

Pegfilgrastim (INN) is a covalent conjugate of recombinant methionyl human G-CSF (filgrastim) and a single 20 kDa monomethoxy-PEG-molecule. The monomethoxy-PEG-molecule is covalently bound to the N-terminal methionyl residue of filgrastim. Pegfilgrastim is marketed in Europe under the trade name Neulasta®.

The principal mode of attachment of PEG, and its derivatives, to peptides is a non-specific bonding through a peptide amino acid residue (see e.g. U.S. Pat. No. 4,088,538, U.S. Pat. No. 4,496,689, U.S. Pat. No. 4,414,147, U.S. Pat. No. 4,055, 635 and WO 87/00056). Another mode of attaching PEG to peptides is through the non-specific oxidation of glycosyl residues on a glycopeptide (see e.g. WO 94/05332).

In these non-specific methods, PEG is added in a random, non-specific manner to reactive residues on a peptide backbone. Random addition of PEG molecules has its drawbacks, including a lack of homogeneity of the final product, and the possibility that the biological or enzymatic activity of the peptide will be reduced. Therefore, during recent years efforts have been made to develop more site specific methods for attaching a synthetic polymer or other label to a peptide and it has been found that specifically conjugated, homogeneous peptide therapeutics can be produced in vitro through the action of enzymes. These enzyme-based conjugations have the advantages of regioselectivity and stereoselectivity. Two principal classes of enzymes for use in the synthesis of conjugated peptides are glycosyltransferases (e.g. sialyltransferases, oligosaccharyltransferases, N-acetylglucosaminyltransferases) and glycosidases. These enzymes can be used for the specific attachment of sugars which can be subsequently modified to comprise a therapeutic moiety. Alternatively, glycosyltransferases and modified glycosidases can be used to directly transfer modified sugars to peptide backbone (see e.g. U.S. Pat. No. 6,399,336 and US 2003/0040037, US 2004/0132640, US 2004/0137557, US 2004/0126838 and US 2004/0142856). Methods combining both chemical and enzymatic synthetic elements are also known (see e.g. US 2004/137557).

The various methods of conjugating polypeptides like G-CSF with polymeric moieties like PEG are well known and extensively described in the prior art. The preparation of glycoPEGylated G-CSF is, for example, described in WO 2005/055946. Another patent application that is directed to the preparation of conjugates between G-CSF and PEG moieties is WO 2006/074467. In this method the conjugates are linked via an intact glycosyl linking group is interposed between and covalently attached to the G-CSF polypeptide and the modifying group. The conjugates are formed from both glycosylated and unglycosylated G-CSF polypeptides by the action of glycosyltransferase. The glycosyltransferase ligates a modified sugar moiety onto either an amino acid or glycosyl residue on the polypeptide. The disclosure of WO 2005/055946 and WO 2006/074467 is explicitly referred to in the context of the present invention.

Besides PEG, also other polymeric moieties have been described as useful conjugates with G-CSF and other therapeutic proteins. WO 02/09766 discloses, among others, biocompatible protein-polymer compounds produced by conjugation of biologically active protein with a biocompatible polymer derivative. The biocompatible polymers used are highly reactive branched polymers, and the resulting conjugates contain a long linker between polymer derivative and protein. Examples of biocompatible polymers according to WO 02/09766 are PEG, PPG, polyoxyethylene (POE), polytrimethylene glycol, polylactic acid and its derivatives, polyacrylic acid and its derivatives, polyamino acids, polyurethane, polyphosphazene, poly(L-lysine), polyalkylene oxide (PAO), water-soluble polymers such as polysaccharide, dextran, and non-immunogenic polymers such as polyvinyl alcohol and polyacryl amide.

WO 94/01483 discloses biocompatible polymer conjugates which are formed by covalently binding a biologically inactive polymer or polymer derivative to a pharmaceutically pure, synthetic hydrophilic polymer via specific types of chemical bonds. As naturally occurring polymers and derivatives thereof, polysaccharides such as hyluronic acid, proteoglycans such as chondroitin sulfates A, B and C, chitin, heparin, heparin sulphate, dextrans such as cyclodextran, hydroxyethyl cellulose, cellulose ether and starch, lipids such as triglycerides and phospholipids are disclosed.

WO 96/11953 describes N-terminally chemically modified protein compounds and methods for their production. Specifically, G-CSF compositions are described which result from coupling a water-soluble polymer to the N-terminus of G-CSF. Examples of water-soluble polymers listed in WO 96/11953 are copolymers of ethylene glycol and propylene glycol, carboxymethyl cellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, PPG homopolymers, polypropylene oxide/ethylene oxide copolymers or polyoxyethylated polyols.

WO 97/30148 describes polypeptide conjugates with reduced allergenicity, comprising a polymeric carrier molecule having two or more polypeptide molecules coupled thereto. These conjugates are produced by activating a polymeric carrier molecule, reacting two or more polypeptide molecules with the activated polymeric carrier molecule and blocking of residual active groups on the conjugate. WO 97/30148 lists a variety of polymeric carrier molecules, including natural or synthetic homopolymers such as polyols, polyamines, polycarboxylic acids and heteropolymers comprising at least two different attachment groups. Examples are given, which comprise star PEGs, branched PEGs, polyvinyl alcohols, polycarboxylates, polyvinylpyrrolidones and poly-D,L-amino acids. The conjugates of WO 97/30148 also include those comprising dextrans such as carboxymethyl dextran, celluloses such as hydroxyethyl cellulose or hydroxypropyl cellulose, hydrolysates of chitosan, starches such as hydroxyethyl starches or hydroxypropyl starches, glycogen, agarose, guar gum, inulin, pullulan, xanthan gum, carrageenin, pectin, alginic acid etc.

WO 03/074087 relates to a method of coupling proteins to a starch-derived modified polysaccharide. The binding action between the protein and the polysaccharide, hydroxyalkyl starch, is a covalent linkage which is formed between the terminal aldehyde group or a functional group resulting from chemical modification of said terminal aldehyde group of the hydroxy alkyl starch molecule, and a functional group of the protein. As reactive group of the protein, amino groups, thio groups and carboxy groups are disclosed.

WO 2005/014050 describe the preparations of conjugates of hydroxyalkyl starch (HAS) and a G-CSF protein, wherein at least one functional group of the polymer or the derivative thereof is reacted with at least one functional group of the protein, thereby forming a covalent linkage. Other prior art documents which relate to the HASylation, preferably HESylation, of polypeptides are WO 2005/014655, WO 2005/092390, WO 2007/031266, WO 2005/092928 and WO 2005/092391.

Although several approaches have been described in the prior art for modifying therapeutic polypeptides such as G-CSF by polymeric moieties in order to prolong its clearance time and to reduce immunogenicity, little work seems to have been done in developing advantageous formulations for such polymer-G-CSF-conjugates.

The above mentioned Neulasta.RTM. product is a liquid composition intended for subcutaneous injection. The preparation comprises pegfilgrastim, sodium acetate, sorbitol, polysorbate 20 and water for injection and has a pH of 4.0 (see <http colon slash slash>www <dot>neulasta <dot>com and ROTE LISTE 2007). The Neulasta.RTM. and Neupogen-.RTM. products, both marketed by Amgen, are almost identical with respect to buffer agent, excipients and pH value of the solution: Neupogen.RTM. comprises filgrastim (instead of pegfilgrastim), sodium acetate, sorbitol, polysorbate 80 and water for injection and has also a pH of 4.0 (see <http colon slash slash>www <dot>neupogen <dot>com and ROTE LISTE 2007).

The present invention is directed to liquid pharmaceutical compositions comprising a polymer-G-CSF-conjugate, wherein the compositions have been specifically developed to take account of the characteristics of polymer-G-CSF-conjugates. Although several approaches have been reported in the prior art with respect to formulations comprising non-conjugated G-CSF, little is known about useful preparations of polymer-G-CSF conjugates.

Though some pharmaceutical compositions developed for non-conjugated G-CSF are presented in the patent literature in such a way as to encompass preparations in which the non-conjugated G-CSF is replaced by a PEG-G-CSF conjugate, it is obvious that the compositions are tailored to, and tested for, unconjugated G-CSF only.

For example, WO 2005/042024 describes stable pharmaceutical compositions comprising G-CSF wherein the composition has a pH value of above 4.0 and further comprises an acid, but is free from surfactants. Although the pharmaceutical composition described in WO 2005/042024 has clearly been developed for non-conjugated G-CSF, it is mentioned in the specification that it also includes G-CSF chemically modified with PEG or the like showing the same or improved biological activity.

Another example is WO 2005/039620 which is also directed to a stable aqueous G-CSF-containing composition. The composition contains succinic acid or tartaric acid or salts thereof as buffer agents and has a preferred pH in the range of 4.0 and 5.8. According to the specification, the G-CSF protein may also be synthetically modified, e.g. by enzymatic glycosylation or chemical PEGylation.

EP 1 260 230 A1 discloses stable protein formulations containing tryptophan as a stabilizer. The list of proteins covers G-CSF, and G-CSF chemically modified with PEG or the like as well. The G-CSF formulations are mentioned to preferably have a pH of 5-7, more preferably 6.0-6.7.

Another example is EP 1 336 410 A1, which describes injectable pharmaceutical formulations containing a physiologically active protein as an active ingredient and at least one sugar as a soothing agent and having a pH of 6.5-7.4. Again in this case, it is mentioned that G-CSF chemically modified with PEG or the like is also included.

EP 1 329 224 A1 describes a G-CSF solution formulation which contains at least one amino acid or a salt thereof, preferably methionine, as a stabilizer. The G-CSF solution formulations preferably have a pH of 5-7, more preferably 5.5-6.8. Again, G-CSF chemically modified with PEG or the like is said to be also included.

However, none of the formulations disclosed in the prior art is a specific polymer-G-CSF-conjugate formulation. Rather, the solutions described in the patent literature have only been developed and tested for unconjugated G-CSF.

The problem underlying the present invention is to provide a polymer-G-CSF-conjugate composition which is adapted to such conjugates and which is stable at elevated temperatures, i.e. above refrigerator temperature which is usually between 2 and 8° C. Further, it is an object of the invention to provide a pharmaceutical composition which does not need reconstitution at any stage of its preparation and which causes as little irritation as possible when administered to a patient.

These problems are solved according to the present invention by providing a pharmaceutical aqueous composition comprising a polymer-G-CSF conjugate, the composition having a pH in the range of 4.5 to 5.5. The aqueous preparation according to the invention comprises a surfactant and optionally one or more other pharmaceutically acceptable excipients. In a preferred embodiment the composition is free from amino acids or derivatives or salts thereof as stabilizers and free from tartaric acid or salts thereof and from succinic acid or salts thereof as buffering agents.

It has surprisingly been found that formulating a polymer-G-CSF conjugate in a composition having a pH value in the range of from 4.5 to 5.5, preferably of 5.0, prevents acid hydrolysis of the conjugate bond. This pH range improves the stability of the solution at temperatures above refrigerator temperature (2-8° C.), especially at room temperature (i.e. below 25° C.) and even at higher temperatures, e.g. 40° C. This means that the composition can be stored without cooling for a prolonged period of time, without significant loss of activity and without significant degradation.

Further, irrespective of storage stability, the compositions according to the invention are advantageous over a comparable composition having a pH of 4.0, since a composition which is less acidic causes less irritation when administered to a patient.

Unless otherwise indicated, the following definitions are set forth to illustrate and define the meaning and scope of the various terms used to describe the invention herein.

The term "polymer-G-CSF conjugate" refers to a conjugate between a G-CSF polypeptide and a polymer wherein the conjugate is formed by a covalent linkage between a functional group of the polymer and a functional group of the polypeptide. The conjugates may comprise one or more polymeric moieties.

The term "G-CSF" (or G-CSF polypeptide or G-CSF protein or G-CSF peptide) refers to a protein having the in vivo biological activity of naturally occurring human G-CSF, i.e. a protein that is capable of stimulating the differentiation and proliferation of hematopoietic progenitor cells. The G-CSF can be unmistakably identified as G-CSF according to the assay described in Stute, N., et al. "Pharmacokinetics of subcutaneous recombinant human granulocyte colony-stimulating factor in children" (1992) Blood 79 (11), pages 2849-2854.

In an exemplary embodiment, G-CSF has an amino acid sequence according to the following SEQ ID NO:1 or SEQ ID NO:2, wherein SEQ ID NO:1 depicts the wild type amino acid sequence of human methionyl-G-CSF as produced in *E. coli*, and SEQ ID NO:2 depicts the amino acid sequence of human G-CSF as produced in mammalian cells, e.g. in CHO cells. SEQ ID NO:1 is the 175 amino acid variant, wherein the first amino acid is methionine and there is a threonine residue at Thr 134. SEQ ID NO:2 is a 174 amino acid variant which has the same sequence as the 175 amino acid variant except that the leading methionine is missing, thus the sequence begins with T and there is a threonine residue at position 133.

```
SEQ ID NO: 1:
MTPLGPASSLPQSFLLKCLEQVRKIQGDGAALQEKLCATYKLCHPEE
LVLLGHSLGIPWAPLSSCPSQALQLAGCLSQLHSGLFLYQGLLQALE
GISPELGPTLDTLQLDVADFATTIWQQMEELGMAPALQPTQGAMPAF
ASAFQRRAGGVLVASHLQSFLEVSYRVLRHLAQP
(175 amino acids)
```

```
                                            SEQ ID NO: 2
TPLGPASSLPQSFLLKCLEQVRKIQGDGAALQEKLCATYKLCHPEEL
VLLGHSLGIPWAPLSSCPSQALQLAGCLSQLHSGLFLYQGLLQALEG
ISPELGPTLDTLQLDVADFATTIWQQMEELGMAPALQPTQGAMPAFA
SAFQRRAGGVLVASHLQSFLEVSYRVLRHLAQP
(174 amino acids)
```

The skilled artisan will readily appreciate that the present invention is not limited to the sequences depicted herein, but also includes variants of G-CSF. Such variants are well known in the art. They may contain deletions, substitutions or additions of one or more amino acids in the above depicted amino acid sequences while maintaining the biological activity of naturally occurring G-CSF. As examples, but in no way meant to be limiting to the present invention, G-CSF variants are described in WO 01/87925, EP 0 456 200 A, U.S. Pat. No. 6,166,183, U.S. Pat. No. 6,004,548, U.S. Pat. No. 5,580,755, U.S. Pat. No. 5,582,823, U.S. Pat. No. 5,675,941, U.S. Pat. No. 5,416,195, U.S. Pat. No. 5,399,345, WO 2005/055946 and WO 2006/074467.

The G-CSF polypeptide may be glycosylated or non-glycosylated. In a preferred embodiment, the G-CSF polypeptide is recombinant human G-CSF produced in *E. coli*, i.e. having the amino acid sequence depicted above in SEQ ID NO:1 or a variant thereof.

The polymer can be any polymer that can be covalently linked to the G-CSF polypeptide and which results in a therapeutically useful polymer-G-CSF-conjugate, when covalently linked to a G-CSF polypeptide. Several suitable polymers have already been mentioned above in the introductory part, these include poly(alkylen glycols), such as PEG and PPG, hydroxyalkyl starches, such as hydroxyethyl starch (HES), and the polymers described in WO 02/09766, WO 96/11953 and WO 97/30148 in connection with polymeric polypeptide conjugates. In a preferred embodiment the polymer is PEG.

All concentration specifications in mg/ml used in the following in connection with the conjugate are related to the G-CSF moiety only. The PEG moiety by definition is not considered for the mass concentration.

While filgrastim has a molecular weight of about 18-19 kD, pegfilgrastim is much larger due to the monomethoxy-PEG moiety and has a molecular weight of about 39 kD. The polymer-G-CSF-conjugates of the present invention may have a molecular weight in the range of 20 to 60 kD, preferably in the range of 35 to 45.

Suitable PEGs are disclosed in the prior art, e.g. in WO 2005/055946, WO 2006/074467 and WO 01/87329. The PEG moiety may be linear or branched and having sizes of 5 to 40 kD. Preferably, the PEG moiety has a molecular weight of 15 to 25 kD, most preferably about 20 kD.

Methods for producing polymer-G-CSF-conjugates have also been described in the prior art. The documents mentioned above in connection with the preparation of conjugates between polypeptides and polymeric moieties are included herewith as references.

Other polymer-G-CSF-conjugates which are useful in the present invention are described in detail in WO 96/11953, EP 822 199 A, WO 01/51510, WO 2006/0128460, EP 921 131 A and EP 744 409. It is herewith explicitly referred to the disclosures of these documents, i.e. to the conjugates and the methods of producing them as described therein.

The skilled artisan will readily appreciate that the present invention is not limited to conjugates wherein a polymer such as PEG or HES is directly linked to an amino acid residue of the protein, but also encompasses conjugates wherein a polymeric moiety and the G-CSF polypeptide are linked to each other via a linker. For example, glycosyl linking groups interposed between the poylpeptide and the PEG moieties are useful linkers within the conjugates of the present invention. WO 2006/074467 describes such polymer-G-CSF conjugates in which the G-CSF polypeptide and the polymeric moiety are linked via a glycosyl linker or via a non-glycosyl linker, e.g. substituted or unsubstituted alkyl, substituted or unsubstituted heteroalkyl. The disclosure of WO 2006/074467 is explicitly included as a reference herewith.

The term "PEG-G-CSF" (PEGylated-G-CSF) refers to a G-CSF protein which is covalently linked with one or more polyethylene glycol moieties as described below. The PEG group(s) and the G-CSF protein may be either linked to each other directly or via a linker, e.g. a glycosyl linker.

In one embodiment of the present invention the polymer-G-CSF peptide conjugate is prepared according to the method described in WO 2006/074467. In a preferred embodiment the polymer-G-CSF peptide is a PEG-G-CSF conjugate having a glycosyl linking group interposed between the PEG modifying moiety and the G-CSF polypeptide. Such a conjugate is referred to as "glycoPEGylated" G-CSF.

In an exemplary embodiment, "glycopeglyated" G-CSF molecules of the invention are produced by the enzyme mediated formation of a conjugate between a glycosylated or non-glycosylated G-CSF peptide and an enzymatically transferable saccharyl moiety that includes a poly(ethylene glycol) moiety within its structure. The PEG moiety is attached to the saccharyl moiety directly (i.e., through a single group formed by the reaction of two reactive groups) or through a linker moiety, e.g., substituted or unsubstituted alkyl, substituted or unsubstituted heteroalkyl, etc. The glycosyl linking group may be sialic acid moieties that are derivatized with PEG.

In a preferred embodiment of the invention the glycosyl linker is bound to the G-CSF protein via O-glycosylation, preferably via O-glycosylation at a threonine residue of the G-CSF protein.

The glycosyl linker preferably comprises a mono-, di- or oligosaccharide, more preferably the glycosyl linker comprises sialic acid and N-acetylgalactosamine. In one embodiment of the present invention the polymer-G-CSF peptide conjugate comprises the moiety:

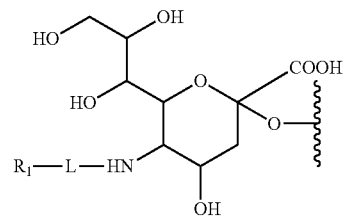

wherein $R_1$ is a moiety comprising a straight-chain or branched poly(ethylene glycol) residue; and L is a linker which is a member selected from a bond, substituted or unsubstituted alkyl and substituted or unsubstituted heteroalkyl; and wherein the peptide is glycosylated with a glycosyl residue and wherein the moiety is covalently bound to the glycosyl residue. The glycosyl residue is preferably N-acetylgalactosamine. In a preferred embodiment, the G-CSF peptide is glycosylated at a threonine residue, preferably at the threonine residue in position 134 (calculated for the methionyl-G-CSF polypeptide, i.e. having an N-terminal methionine and 175 amino acids in total). In a preferred embodiment, $R_1$ is a straight-chain poly(ethylene glycol) residue, and L is a heteroalkyl.

The G-CSF peptide conjugate described above can be produced according to a method comprising (a) contacting a substrate G-CSF peptide with a PEG-sialic acid donor having the formula:

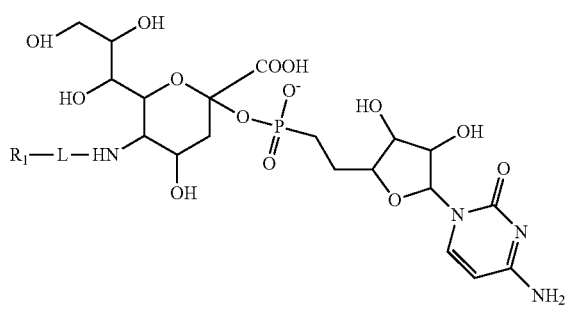

wherein $R_1$ and L are as defined above, and an enzyme that is capable of transferring the PEG-sialic acid moiety from the donor onto the glycosyl residue of the substrate G-CSF peptide. In a preferred embodiment, the enzyme is a sialyltransferase, e.g. ST6GalNAcI, as described in WO 2005/055946.

The G-CSF peptide conjugate described above can be produced according to a method comprising (a) contacting an unglycosylated substrate G-CSF peptide with a glycosyl donor and an enzyme that is capable of transferring the glycosyl moiety from the donor onto the substrate G-CSF peptide, and (b) contacting the glycosylated G-CSF peptide with a PEG-sialic acid donor having the formula:

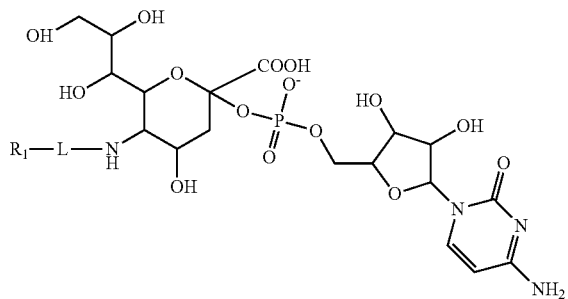

wherein $R_1$ and L are as defined above, and an enzyme that is capable of transferring the PEG-sialic acid moiety from the donor onto the glycosyl residue of the substrate G-CSF peptide, wherein (a) and (b) are either sequential or simultaneous reactions. In a preferred embodiment the glycosyl donor is UDP-N-acetylgalactosamine. In a preferred embodiment the enzyme in (a) is an N-acetylgalactosaminyltransferase and the enzyme in (b) is a sialyltransferase, e.g. GalNAcT2 in (a) and ST6GalNAcI in (b).

The G-CSF can be produced by chemical synthetic procedures or can be of any human or another mammalian source and can be obtained by purification from naturally occurring sources like human placenta, human blood or human urine. In addition, a lot of epithelial carcinomas, acute myeloid leukaemia cells and various tumor cell lines are capable of expressing this factor.

Preferably, the G-CSF is recombinantly produced. This includes prokaryotic or eukaryotic host expression of exogenous DNA sequences obtained by genomic or cDNA cloning or by DNA synthesis. Suitable prokaryotic hosts include various bacteria such as *E. coli*, which is the preferred host. Suitable eukaryotic hosts include yeast such as *S. cerevisiae* and mammalian cells such as Chinese hamster ovary (CHO) cells and monkey cells.

The recombinant production of a protein such as G-CSF is known in the art. In general, this includes the transfection of host cells with an appropriate expression vector, the cultivation of the host cells under conditions which enable the production of the protein and the purification of the protein from the host cells. For detailed information see e.g. Souza, L. M. et al. 1986, Recombinant human granulocyte colony-stimulating factor: effects on normal and leukemic myeloid cells, Science (1986) 232: 61-65; Nagata, S. et al. 1986, Molecular cloning and expression of cDNA for human granulocyte colony-stimulating factor, Nature (1986) 319: 415-418; Komatsu, Y. et al. 1987, Cloning of granulocyte colony-stimulating factor cDNA from human macrophages and its expression in *Escherichia coli*, Jpn. J. Cancer Res. (1987) 78: 1179-1181.

In a preferred embodiment, the G-CSF has the amino acid sequence of human mature G-CSF (see e. g.; Nagata, S. et al. (1986), vide supra), and may further contain a methionine at its amino terminus, which then results in a protein of 175 amino acids (see SEQ ID NO: 1 above). Furthermore, instead of the methionine, G-CSF may contain a serine or a threonine residue.

The protein is then purified according to a conventional downstream processing protocol. Suitable purification methods for G-CSF are described in the prior art, e.g. in WO 87/01132, EP 0 719 860 A, EP 1 458 757 A, EP 1 527 188 A, WO 03/051922, WO 01/04154 and WO 2006/097944.

In one embodiment of the present invention the polymer-G-CSF peptide conjugate is prepared as described in Example 1 provided herein. This conjugate is characterized in that the G-CSF polypeptide and the PEG moiety are linked via an N-acetylgalactosaminyl (GalNAc) group and a sialic acid (SA) group. The conjugate has the structure: G-CSF-GalNAc-SA-PEG as follows:

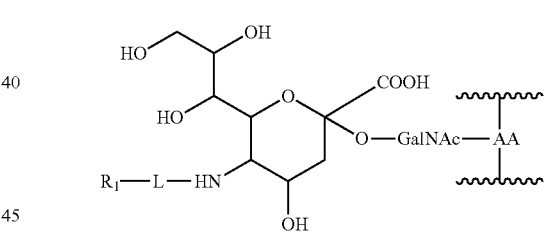

wherein $R_1$ and L are as defined above and AA is an amino acid residue of G-CSF.

In an exemplary embodiments, R1 is a linear PEG moiety linked via a sialic acid group and a GalNAc group to a G-CSF polypeptide as shown below:

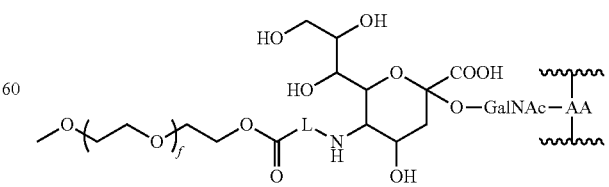

wherein L is as defined above; AA is an amino acid residue of G-CSF; and f is an integer selected from 1 to 2500.

In certain embodiments, the polymer G-CSF conjugate has the following formula:

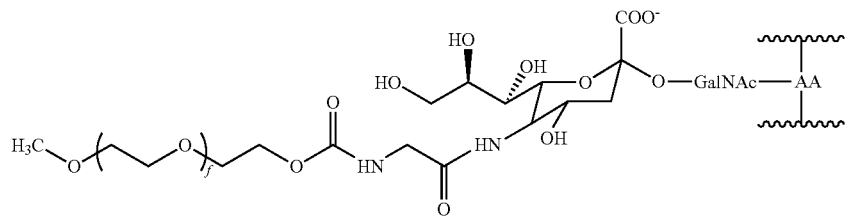

wherein AA is threonine 133 (threonine 134 if an N-terminal methionine is present) of G-CSF; and f is an integer selected from 1 to 2500.

The pharmaceutical preparation of the present invention is a liquid composition, e.g. an aqueous solution. For injection purposes, the use of pure water as solvent is preferred. Other solvents which are suitable and conventional for pharmaceutical preparations can, however, also be employed. In a preferred embodiment of the invention, the pharmaceutical compositions are isotonic solutions.

Further, there is no need for reconstitution at any stage of the preparation of the liquid solution formulation of the invention. The solution is a ready-to-use formulation.

The pharmaceutical composition of the invention has a pH in the range of 4.5 to 5.5. In a preferred embodiment, the pH value is between 4.7 to 5.3, more preferably between 4.8 to 5.2 and most preferably between 4.9 and 5.1.

If an adjustment is required in order to achieve the desired pH range, the pH value is adjusted by means of suitable solutions; with acidic solutions in case a reduction of the pH value is indicated and with alkaline solutions in case an increase of the pH value is indicated. Suitable acidic solutions are e.g. hydrochloric acid, phosphoric acid, citric acid and sodium or potassium hydrogen phosphate. Suitable alkaline solutions are alkali and alkali earth hydroxides, alkali carbonates, alkali acetates, alkali citrates and dialkali hydrogen phosphates, e.g. sodium hydroxide, sodium acetate, sodium carbonate, sodium citrate, disodium or dipotassium hydrogen phosphate or ammonia.

Preferably, the pH of the solution is adjusted using sodium hydroxide. As a consequence, the formulation of the invention may contain sodium ions. Sodium is usually present in a concentration of less than 10 mmol/l, typically less than 6 mmol/l.

The pharmaceutical preparation of the invention comprises one or more surfactants. Typical examples of surfactants include: nonionic surfactants, eg, sorbitan fatty acid esters such as sorbitan monocaprylate, sorbitan monolaurate, sorbitan monopalmitate; glycerin fatty acid esters such as glycerin monocaprylate, glycerin monomyristate, glycerin monostcarate; polyglyccrin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having an HLB of 6-18; anionic surfactants, eg, alkyl sulfates having a C10-18 alkyl group such as sodium cetylsulfate, sodium laurylsulfate, sodium oleylsulfate; polyoxyethylene alkyl ether sulfates having an average EO mole number of 2-4 and a C10-18 alkyl group such as sodium polyoxyethylene laurylsulfate; alkyl sulfosuccinic acid ester salts having a C8-18 alkyl group such as sodium laurylsulfosuccinate; and natural surfactants, eg, lecithin; glycerophospholipids; sphingophospholipids such as sphingomyelin; sucrose fatty acid esters of C12-18 fatty acids. One or more of these surfactants may be added in combination to formulations of the present invention.

Preferred surfactants are polyoxyethylene sorbitan alkyl esters, more preferably Polysorbates 20, 21, 40, 60, 65, 80, 81, 85, most preferably Polysorbates 20 and 80.

The concentration of the detergent in the formulation is typically in the range of from 0.0005% (w/v) to 0.05% (w/v), preferably from 0.001% (w/v) to 0.01% (w/v), more preferably from 0.002% (w/v) to 0.006% (w/v) and most preferably from 0.003% (w/v) to 0.004% (w/v), based on the total volume of the solution formulation.

Usually the formulations of the invention contain the surfactant Polysorbate 20 or 80 in a concentration of 0.003% (w/v), 0.0033% (w/v) or 0.004% (w/v). Polysorbate 20 is preferred.

The formulation according to the invention comprises a physiologically acceptable buffering agent. Suitable buffers are known in the art of solution formulations, e.g. phosphate buffers (preferably sodium monohydrogen phosphate—sodium dihydrogen phosphate system), citrate buffers, lactate buffers, acetate buffers, carbonate buffers, BisTris, MES, and Glycine-HCl. The use of an acetate buffer, i.e. acidic acid or a salt thereof, e.g. alkali or ammonium salts, is preferred.

The buffering agent is usually present in the formulation in a concentration of 1 to 100 mmol/l, preferably 2 to 50 mmol/l and most preferably 5 to 20 mmol/l. In a preferred embodiment the buffer is present at 10 mmol/l, most preferably it is acetate present at 10 mmol/l.

The concentration of the buffer, e.g. acetate, is chosen in such a way that the pH stabilizing action as well as sufficient buffering capacity is provided. However, simultaneously the ion concentration and hence the conductivity of the solution are kept as low as possible in order to avoid the formation of aggregates.

In an embodiment of the invention the conductivity of the final solution formulation is less than 1.0 mS/cm, preferably less than 0.8 mS/cm and more preferably less than 0.5 mS/cm.

Further, it is preferred that the preparation is free from tartaric acid and succinic acid and salts thereof. It is also preferred that the solution is free from HEPES, TES and tricine.

It is also preferred that the formulation of the invention is free from sulphate ions.

Further, in a preferred embodiment, the formulation is free from preservatives, wherein preservatives are meant to be substances, which are conventionally used as preservatives for increasing storage stability and which, in standard concentrations, have a bactericidal effect. In particular, the formulation does not contain preservatives like chloroethane, benzyl alcohol, p-chloro-m-cresol, and pyrocarbonic acid dialkyl ester, and benzalkonium chloride.

In an embodiment of the invention, the formulation further comprises a polyol, preferably a sugar alcohol, most preferably mannitol or sorbitol as a tonicity modifying agent. Sorbitol is especially preferred. The amount of sugar such as sorbitol or mannitol is usually up to 10.0% (w/v), based on the total volume of the solution. Preferably, the concentration is up to 8.0% (w/v), more preferably up to 6.0% (w/v) and most preferably 5.0% (w/v). In a preferred embodiment, sorbitol is present in an amount of 5.0% (w/v).

Further, it is preferred that the solution formulation of the invention does not contain a stabilising agent selected from amino acids, derivatives and salts thereof, polymeric stabilising agents and proteinaceous stabilising agents.

The polymer-G-CSF conjugate containing formulations of the present invention are normally administered via parenteral routes such as injection (subcutaneous, intravenous or intramuscular injection) or percutaneous, mucosal, nasal or pulmonary administration, but may also be orally administered.

The polymer-G-CSF conjugate is usually present in the formulation in a concentration of from 1.0 to 30.0 mg/ml, preferably from 5.0 to 20.0 mg/ml and most preferably from 8.0 to 12.0 mg/ml. In a preferred embodiment, the polymer-G-CSF conjugate is PEG-SA-GalNAc-G-CSF present in an amount of 10.0 mg/ml.

In a preferred embodiment the formulation comprises the polymer-G-CSF conjugate as active ingredient, a surfactant, a buffering agent, a tonicity modifying agent, sodium ions and water, and no other constituent. Most preferably the aqueous preparation according to the invention contains a glycoPEGylated G-CSF as active agent, Polysorbate 20 and/or Polysorbate 80 as surfactant, sorbitol and/or mannitol as tonicity modifier, acetate as buffer and sodium, and no other excipients.

In another aspect of the invention the aqueous preparation of the invention as described above is diluted to obtain an aqueous dilution preparation that is suited for pediatric use. Appropriate dilutions for the treatment of children are obtained by diluting the above described solution of the invention 1:2 to 1:8.

The invention also relates to a pharmaceutical container containing the aqueous preparation of the invention or a dilution solution obtained therefrom by dilution. Suitable pharmaceutical containers are known from the prior art. The container may, for example, be a syringe, vial, infusion bottle, ampoule or carpoule. In a preferred embodiment, when the container is a syringe, the syringe is equipped with a needle protection system. Such needle protection systems which are well known from the prior art help to reduce the risk of injuries. In another embodiment, the container is a carpoule within an injection pen.

The present invention also relates to a method of preparing an aqueous preparation of the invention, wherein the polymer-G-CSF conjugate as the active agent is formulated in an aqueous preparation having a pH in the range of 4.5 to 5.5 and comprising a surfactant and further pharmaceutical excipients.

In another aspect the invention relates to the use of an aqueous preparation of the invention in the treatment or prevention of neutropenia. Further, the aqueous preparation of the invention can be advantageously used in the treatment or prevention of neurological disorders or in connection with bone marrow transplantation. In general, the pharmaceutical solutions of the invention are useful for stem cell mobilization.

The pharmaceutical liquid formulation according to the invention was found to exhibit a very good storage stability. Within the scope of the present invention, the term "storage stable" is understood to mean that the content of active polymer-G-CSF conjugate still amounts to 80% or more of the initial concentration after three months of storage of the formulation at 25° C. Preferably, after storage for three months at 25° C., the remaining content of G-CSF activity still amounts to at least 85%, more preferably at least 90%, and most preferably at least 95% of the original activity.

The activity of the polymer-G-CSF conjugate can be determined by means of conventional activity tests, as they are described in the prior art for G-CSF; see e.g. Draft Monographie "Filgrastim Concentrated Solution" PharmEur. Vol. 19, No. 1, January 2007, or Stute, N., et al. "Pharmacokinetics of subcutaneous recombinant human granulocyte colony-stimulating factor in children 1" (1992) Blood 79 (11), pages 2849-2854.

The measurement of G-CSF activity in vitro is e.g. described by Shirafuji, N. et al. 1989, A new bioassay for human granulocyte colony-stimulating factor (hG-CSF) using murine myeloblastic NFS-60 cells as targets and estimation of its levels in sera from normal healthy persons and patients with infectious and hematological disorders, Exp. Hematol. (1989) 17, 116-119. For the measurement of G-CSF activity in vivo see e.g. Tanaka, H. et al. 1991, Pharmacokinetics of recombinant human granulocyte colony-stimulating factor conjugated to polyethylene glycol in rats, Cancer Research (1991) 51, 3710-3714. Further publications where tests for the measurement of the activity of G-CSF are described are U.S. Pat. No. 6,555,660; Nohynek, G. J. et al.1997, Comparison of the potency of glycosylated and non-glycosylated recombinant human granulocyte colony-stimulating factors in neutropenic and non-neutropenic CD rats, Cancer Chemother. Pharmacol. (1997) 39, 259-266.

The purity of the polymer-G-CSF conjugate used in the formulation according to the invention should be at least 95%, preferably at least 97, more preferably at least 99% and most preferably more than 99%. The degree of purity can be determined by means of HPLC analysis. Suitable materials and protocols for conducting such analyses can be obtained from commercial suppliers such as Vydac or TOSOH Bioscience (<http colon slash slash>www <dot>tosohbiosep <dot>de).

The components for formulating the solutions according to the invention can be obtained from conventional sources, for example from companies such as Sigma or Merck.

The production of the formulation of the invention can be performed according to conventional methods. The components of the formulation can be dissolved in an aqueous buffer. Alternatively, the conjugate can already be obtained in an aqueous buffer as the result of the purification process.

Finally, the finished liquid formulation is filled into a suitable pharmaceutical container, where it is stored until administration.

The following Examples are intended to illustrate the invention without limiting its scope.

EXAMPLES

Example 1

Preparation of G-CSF-GalNAc-SA-PEG

The following example illustrates the preparation of G-CSF-GalNAc-SA-PEG in (a) a two sequential step method wherein each intermediate product is purified before it is used in the next step, and (b) a one step method using simultaneous addition of enzymes a. The Two Step Method Preparation of G-CSF-GalNAc (pH 6.2) from G-CSF and UDP-GalNAc Using GalNAc-T2.

G-CSF (960 µg) in 3.2 mL of packaged buffer was concentrated by utrafiltration using an UF filter (MWCO 5K) and then reconstituted with 1 mL of 25 mM MES buffer (pH 6.2, 0.005% $NaN_3$). UDP-GalNAc (6 mg, 9.24 mM), GalNAc-T2 (40 µL, 0.04 U), and 100 mM $MnCl_2$ (40 µL, 4 mM) were then added and the resulting solution was incubated at room temperature.

After 24 hrs, MALDI indicated the reaction was complete. The reaction mixture was directly subjected to HPLC purification using SEC (Superdex 75 and Superdex 200) and an elution buffer comprising of PBS (phosphate buffered saline, pH 4.9 and 0.005% Tween 80). The collected peak of G-CSF-GalNAc was concentrated using a Centricon 5 KDa MWCO filter to about 150 µL and the volume adjusted to 1 ml using PBS (phosphate buffered saline, pH 4.9 and 0.005% Tween 80). Final protein concentration 1 mg/mL ($A_{280}$), yield 100%. The sample was stored at 4° C.

Preparation of G-CSF-GalNAc-SA-PEG Using Purified G-CSF-GalNAc, CMP-SA-PEG (20 KDa) and Mouse ST6GalNAc-TI (pH 6.2).

The G-CSF-Gal NAc solution containing 1 mg of protein was buffer exchanged into 25 mM MES buffer (pH 6.2, 0.005% $NaN_3$) and CMP-SA-PEG (20 KDa) (5 mg, 0.25 µmol) was added. After dissolving, $MnCl_2$ (100 µL, 100 mM solution) and ST6Gal NAc-I (100 µL, mouse enzyme) was added and the reaction mixture rocked slowly at 32° C. for three days. The reaction mixture was concentrated by ultrafiltration (MWCO 5K) and buffer exchanged with 25 mM NaOAc (pH 4.9) one time and then concentrated to 1 mL of total volume. The product was then purified using SP-Sepharose (A: 25 mM NaOAc+0.005% tween-80 pH 4.5; B: 25 mM NaOAc+0.005% Tween-80 pH 4.5+2M NaCl) at retention time 13-18 mins and SEC (Superdex 75; PBS-pH 7.2, 0.005% Tween 80) at retention time 8.6 mins (Superdex 75, flow 1 ml/min) The desired fractions were collected, concentrated to 0.5 mL and stored at 4° C.

b. One Step Method

One Pot Process Using Mouse ST6GalNAc-I (pH 6.0).

G-CSF (960 µg of protein dissolved in 3.2 mL of the product formulation buffer) was concentrated by ultrafiltration (MWCO 5K) to 0.5 ml and reconstituted with 25 mM MES buffer (pH 6.0, 0.005% $NaN_3$) to a total volume of about 1 mL or a protein concentration of 1 mg/mL. UDP-GalNAc (6 mg, 9.21 µmol), GalNAc-T2 (80 µL, 80 mU), CMP-SA-PEG (20 KDa) (6 mg, 0.3 µmol) and mouse enzyme ST6GalNAc-I (120 µL) and 100 mM $MnCl_2$ (50 µL) were then added. The solution was rocked at 32° C. for 48 hrs and purified using standard chromatography conditions on SP-Sepharose. A total of 0.5 mg of protein ($A_{280}$) was obtained or about a 50% overall yield. The product structure was confirmed by analysis with both MALDI and SDS-PAGE.

One Pot Process Using Chicken ST6GalNAc-I (pH 6.0).

14.4 mg of G-CSF; was concentrated to 3 mL final volume, buffer exchanged with 25 mM MES buffer (pH 6.0, 0.05% $NaN_3$, 0.004% Tween 80) and the volume was adjusted to 13 mL. The UDP-GalNAc (90 mg, 150 µmole), GalNAc-T2 (0.59 U), CMP-SA-PEG-20 KDa (90 mg), chicken ST6GalNAc-I (0.44 U), and 100 mM $MnCl_2$ (600 µL) were then added. The resulting mixture stood at room temperature for 60 hrs. The reaction mixture was then concentrated using a UF (MWCO 5K) and centrifugation. The residue (about 2 mL) was dissolved in 25 mM NaOAc buffer (pH 4.5) and concentrated again to 5 mL final volume. This sample was purified using SP-Sepharose for about 10-23 min, SEC (Superdex 75, 17 min, flow rate 0.5 ml/min) and an additional SEC (Superdex 200, 23 min, flow rate 0.5 ml/min), to yield 3.6 mg (25% overall yield) of G-CSF-GalNAc-SA-PEG-20 KDa ($A_{280}$ and BCA method).

Example 2

Liquid Polymer-G-CSF Conjugate (PEG-SA-GalNAc-G-CSF) Formulation

A liquid formulation comprising glycoPEGylated G-CSF (the conjugate having the structure: PEG-SA-GalNAc-G-CSF) was prepared by formulating the following components in an aqueous acetate buffer solution.

| Ingredient | |
| --- | --- |
| glycoPEGylated G-CSF | 10 mg/ml |
| Acetate | 10 mM |
| Sorbitol | 5.0% (w/v) |
| Polysorbate 20 | 0.0033% (w/v) |
| Sodium | 4.38 mM |
| pH | 5.0 |

The pH value of the composition was adjusted by adding NaOH. All ingredients are of a quality according to the European Pharmacopoeia (Ph. Eur.).

In addition, the same composition was prepared having either pH 4.5 or pH 5.5 and proportionately less or more sodium, respectively. A comparative formulation was also prepared which has a pH of 4.0 (like that of the Neulasta® preparation).

Example 3

Stability Tests of the Formulations According to the Present Invention

The compositions, pH 4.5, 5.0 and 5.5, were aliquoted in 500 µl/vial and stored at 2-8° C. and at 25° C.). After 1, 2, 3, 4.5, 6, 8, 12, and 15 months samples were tested for the test parameters given in the table below.

The expected specifications were as follows for the composition having a pH of 5.0:

| Test parameter | Method | Specification |
| --- | --- | --- |
| Appearance | Visual inspection | Clear colorless |
| Content | UV-VIS | 10.0 mg/ml ± 5% |
| Content | RP-HPLC (30° C.) | 10.0 mg/ml ± 5% |
| Potency | Bioassay | 54-156% |
| Identity | SDS-PAGE | Conforms to reference standard |
| Purity | Western Blot | Conforms to reference standard |
| Purity | RP-HPLC (60° C.) | Oxidation <2.0% |
| Purity | RP-HPLC (30° C.) | Non pegylated G-CSF 2.0% |
| Purity | SEC | Dimers and aggregates <2.0% |
| Deamidation | IEF | No additional bands detectable |
| pH | According to Ph. Eur. 5 and USP 28 | 5.0 ± 0.2 |
| Endotoxins | Test for bacterial endotoxins according to Ph. Eur. 5 | <5 EU/mg |
| Sterility | According to Ph. Eur. 5 | Sterile |
| Sub-visible particles | Particulate contamination: sub-visible particles according to Ph. Eur. 5 | <6000 particles ≥ 10 μm per vial; <600 particles ≥ 25 μm per vial |

All samples tested at T=0, 1 month, 2 months, 3 months, 4.5 months, 6 months, 8 months, 12 months and 15 months fulfilled the expected specifications. This was found for all tested compositions comprising glycoPEGylated G-CSF and having a pH of 4.5, 5.0 or 5.5.

The compositions of the invention were compared with two comparative formulations: Neulasta® (pH 4.0) and a composition of glycoPEGylated G-CSF (PEG-SA-GalNAc-G-CSF) having a pH of 4.0. The results show that in comparison with the comparative solution comprising glycoPEGylated G-CSF and having a pH of 4.0, the formulations having higher pH values of 4.5, 5.0 and 5.5 show better storage stability. The collected data allow the conclusion that the higher pH values prevent acid hydrolysis of the glycoPEG bond. Further, it was observed that the formulations of the present invention have a stability that is comparable to the stability of the PEG-G-CSF conjugate known as Nculasta®.

The invention claimed is:

1. An aqueous preparation comprising a polymer-G-CSF conjugate, wherein the preparation has a pH in the range of 4.5 to 5.5 and further comprises a surfactant, wherein the polymer and G-CSF are linked via a glycosyl linker, and wherein the preparation is free from sulfate ions.

2. Aqueous preparation according to claim 1, wherein the polymer is polyalkylene glycol.

3. Aqueous preparation according to claim 1, wherein the glycosyl linkage is via O-glycosylation.

4. Aqueous preparation according to claim 3, wherein the O-glycosylation is at a threonine residue of the G-CSF protein.

5. Aqueous preparation according to claim 4, wherein the threonine residue is Thr 134 based on the amino acid sequence of methionyl-G-CSF protein or Thr 133 based on the amino acid sequence of naturally occurring human G-CSF.

6. Aqueous preparation according to claim 1, wherein the glycosyl linker comprises a mono-, di- or oligosaccharide.

7. Aqueous preparation according to claim 1, wherein the glycosyl linker comprises sialic acid and N-acetylgalactosamine.

8. Aqueous preparation according to claim 1, wherein the surfactant is present in a concentration of 0.0001% (w/v)-0.05% (w/v).

9. Aqueous preparation according to claim 1, wherein the surfactant is a polyoxy ethylene sorbitan alkyl ester.

10. Aqueous preparation according to claim 9, wherein the polyoxy ethylene sorbitan alkyl ester is Polysorbate 20 or Polysorbate 80.

11. Aqueous preparation according to claim 1, wherein the pH is in the range of 4.7 to 5.3.

12. Aqueous preparation according to claim 1, wherein the pH is in the range of 4.9 to 5.1.

13. Aqueous preparation according to claim 1, further comprising a physiologically acceptable buffering agent.

14. Aqueous preparation according to claim 13, wherein the buffering agent comprises acetic acid or a salt thereof.

15. Aqueous preparation according to claim 13, wherein the buffering agent is present in a concentration of 2-50 mmol/l.

16. Aqueous preparation according to claim 1, further comprising a tonicity modifying agent selected from sorbitol and mannitol.

17. Aqueous preparation according to claim 1, wherein the tonicity modifying agent is present in a concentration of 1-10%.

18. Aqueous preparation according to claim 1, wherein the preparation is free from stabilising agents selected from amino acids, polymeric stabilising agents and proteinaceous stabilising agents.

19. Aqueous preparation according to claim 1, wherein the preparation is free from preservatives.

20. Aqueous preparation according to claim 1, wherein the pH is adjusted using NaOH.

21. Aqueous preparation according to claim 1, wherein the preparation contains sodium ions.

22. Aqueous preparation according to claim 1, wherein the preparation contains a polymer-G-CSF conjugate as active agent, Polysorbate 20 and/or Polysorbate 80 as surfactant, sorbitol and/or mannitol as tonicity modifier, acetate as buffer and sodium, and no other excipients.

23. Aqueous preparation according to claim 1, wherein the polymer-G-CSF conjugate is present in a concentration of 1-20 mg/ml.

24. Aqueous preparation according to claim 1, wherein the polymer-G-CSF conjugate is present in a concentration of 8-12 mg/ml.

25. Aqueous dilution preparation derived from the aqueous preparation according to claim 1, wherein the aqueous preparation is diluted 1:2 to 1:8.

26. Pharmaceutical container containing an aqueous preparation according to claim 1.

27. Pharmaceutical container according to claim 26, wherein the container is a syringe, vial, infusion bottle, ampoule or carpoule.

28. Pharmaceutical container according to claim 26, wherein the container is a syringe equipped with a needle protection system.

29. Pharmaceutical container according to claim 26, wherein the container is a carpoule within an injection pen.

30. Process for preparing an aqueous preparation according to claim 1, wherein the polymer-G-CSF conjugate as the active agent is formulated in an aqueous preparation having a pH in the range of 4.5 to 5.5 and comprising a surfactant and further pharmaceutical excipients.

\* \* \* \* \*

UNITED STATES PATENT AND TRADEMARK OFFICE
CERTIFICATE OF CORRECTION

PATENT NO.       : 8,546,328 B2  
APPLICATION NO. : 12/675749  
DATED            : October 1, 2013  
INVENTOR(S)      : Hinderer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 464 days.

Signed and Sealed this
Fifteenth Day of September, 2015

Michelle K. Lee
*Director of the United States Patent and Trademark Office*